United States Patent
Jung et al.

[11] Patent Number: 5,965,762
[45] Date of Patent: Oct. 12, 1999

[54] CHLOROHYDROSILANE DERIVATIVES AND THEIR PREPARATION METHOD

[75] Inventors: Il Nam Jung, Seoul; Bok Ryul Yoo, Koyang; Joon Soo Han; Weon-Cheol Lim, both of Seoul, all of Rep. of Korea

[73] Assignee: Korea Institute of Science and Technology, Seoul, Rep. of Korea

[21] Appl. No.: 09/112,590

[22] Filed: Jul. 9, 1998

[30] Foreign Application Priority Data

Aug. 1, 1997 [KR] Rep. of Korea .................. 97-36920

[51] Int. Cl.⁶ ........................................... C07F 7/08
[52] U.S. Cl. ............................ 556/487; 556/474
[58] Field of Search ..................... 556/487, 474

[56] References Cited

U.S. PATENT DOCUMENTS

| | | | |
|---|---|---|---|
| 4,097,511 | 6/1978 | Berger | 556/487 |
| 5,386,050 | 1/1995 | Jung et al. | |
| 5,527,938 | 6/1996 | Jung et al. | 556/487 |
| 5,556,822 | 9/1996 | Jung et al. | |
| 5,646,326 | 7/1997 | Schuler | 556/487 X |

OTHER PUBLICATIONS

H.E. Opitz et al. The Preparation of Monobromosilane and Organic Silyl Derivatives, J.Am.Chem.Soc. 78, 292 (1956).
F.C. Whitmore et al. Hydrogen–Halogen Exchange Reactions of Triethylsilane, J.Am.Chem.Soc. 69, 2108 (1947).
S.N. Borisov et al. Doklady Acad. Nauk SSSR 114, 93 (1957).
V.V. Ponomarev et al. Izv.Acad. Nauk SSSR, Ser.Khim, 1972, 1379.

*Primary Examiner*—Paul F. Shaver
*Attorney, Agent, or Firm*—Darby & Darby

[57] ABSTRACT

New chlorohydrosilane derivatives having the general formula (I) and preparation method thereof. The chlorohydrosilane derivatives (I) of the present invention which have both Si—Cl and Si—H bonds are prepared by partially reducing chlorosilane of the formula (II) which have at least two Si—Cl bonds with lithiumaluminum hydride. The chlorohydrosilane derivatives (I) of the present invention, which have both Si—H and Si—Cl bonds in a molecule can be advantageously used in preparing various compounds because a Si—H bond enables the hydrosilylation with unsaturated organic compounds, while a Si—Cl bond can participate in hydrolysis or in a reaction with a nucleophilic compound such as Grignard reatent:

$$R^1R^2SiHCl \quad (I)$$

$$R^1R^2SiCl_2 \quad (II)$$

wherein $R^1$ is straight, branched, or cyclic alkyl group having 1 to 30 carbon atoms, which can include an aromatic group or heterocyclic group, and $R^2$ represents chloro group, or straight, branched, or cyclic alkyl group having 1 to 30 carbon atoms, which can include an aromatic group or heterocyclic group.

3 Claims, No Drawings

CHLOROHYDROSILANE DERIVATIVES AND THEIR PREPARATION METHOD

BACKGROUND OF THE INVENTION

The present invention relates to the new chlorohydrosilane derivatives having the following formula (I) and a preparation method thereof. The chlorohydrosilane derivatives of the formula (I) of the present invention which have both of the Si—H and Si—Cl bonds in their molecular structures are prepared by reacting chlorosilane of the following formula (II) which has at least two Si—Cl bonds with lithium aluminum hydride (LiAlH$_4$). Because a Si—H bond enables the hydrosilylation reaction with the unsaturated organic compounds and a Si—Cl bond can participate in hydrolysis or the reaction with a nucleophilic compound such as Grignard reatent, the chlorohydrosilane derivatives of the present invention which have both of the aforementioned bonds are important organo silane compounds which can be employed in manufacturing various compounds.

$$R^1R^2SiHCl \qquad (I)$$

$$R^1R^2SiCl_2 \qquad (II)$$

wherein R$^1$ is straight, branched or cyclic alkyl group having 1 to 30 carbon atoms which can include an aromatic group or heterocyclic group, and R$^2$ represents chloro group, straight, branched, or cyclic alkyl group alkyl group having 1 to 30 carbon atoms, which can include an aromatic group or heterocyclic group.

Generally, a Si—Cl bond is converted into a Si—H bond by using a reducing agent such as lithiumaluminumhydride (C. Eaborn, "Organosilicon Compounds", Academic Press Inc., New York, 1960). A typical method comprises drop addition of silane compounds into a flask which contain lithiumaluminum hydride in a solvent such as ethylether or tetrahydrofuran in a room temperature or under reflux temperature.

$$4Me_3SiCl + LiAlH_4 \rightarrow 4Me_3SiH + LiAlCl_4$$

It has been known to be difficult to partially reduce a halogen group of a silicon compound having at least two halogen groups by using lithiumaluminum hydride. McCusker and his colleagues reported that although they tried to prepare chlorohydrosilane by partially reducing an excess amount of ethyltribromosilane with a small amount of lithiumaluminum hydride at low temperature, only they obtained were totally reduced ethylsilanes [P. A. McCusker and E. L. Reilly, J. Am. Chem. Soc.,75, 1583(1953)].

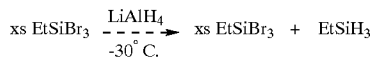

In addition, Opitz and his colleagues reported that they failed to get partially-reduced chlorohydrosilane even though they reacted an excess amount of tetrachlorosilane by using lithiumaluminumhydride or calciumhydride at low temperature [H. E. Opitz J. S. Peake and W. H. Nebergall, J. Am. Chem. Soc., 78, 292 (1956)].

The redistribution reaction of a silicon compound is a reaction wherein each of the hydrogen, halogen, phenyl, or alkyl group attached to silicon are mutually exchanged in the presence of a metal catalyst.

Whitmore and his colleagues reported on the synthesis of diethylchlorosilane and diethylsilane by redistribution of diethyldichlorosilane and triethylsilane in the presence of aluminum chloride catalyst. (F. C. Whitmore, E. W. Pietrusza, and L. H. Sommer, J. Am. Chem. Soc. 69, 2108(1947)).

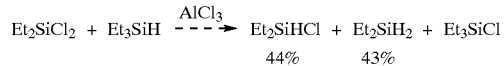

In addition, Borisov and colleagues reported that exchange reaction of Si—H and Si—Cl easily occurs in the presence of aluminum chloride catalyst. (S. N. Borisov, M. G. Voronkov, and B. N. Dolgov, *Doklady Akad. Nauk S.S.S.R.* 114, 93(1957)).

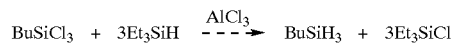

In another example, Ponomarev and his colleagues reported that the reaction of phenylchlorosilane and methylchlorosilane at 250°C. in the presence of lithiumaluminum hydride catalyst resulted in the redistribution into the compounds having both phenyl group and methyl group. (V. V. Ponomarev, V. N. Penskii, S. A. Golubtsov, K. A. Andrianov, and E. N. Chekrii, *Izv. Akad. Nauk SSSR, Ser. Khim.* 1972, 1379)

While studying the partial reduction of chlorosilane compounds with the known reaction as aforementioned, the present inventors have found that a partially reduced silane compound can be obtained as a main product in case the lithiumaluminum hydride and chlorosilane compound are reacted at high temeprature without using solvent.

The compounds of general formula (I) are very important intermediates in organosilicon chemistry, because Si—H of the general formula (I) compounds makes it possible to easily introduce an organic group through the hydrosilylation with unsaturated organic compounds.

The inventors of the present invention previously invented a preparation method of a new (2-arylpropyl)alkylsilane derivatives by hydrosilylating (2-arylpropyl)silane derivatives and olefin compounds (I. N. Jung, B. R. Yoo, B. W. Lee, S. H. Yeon, U.S. Pat. No. 5,386,050(1995)).

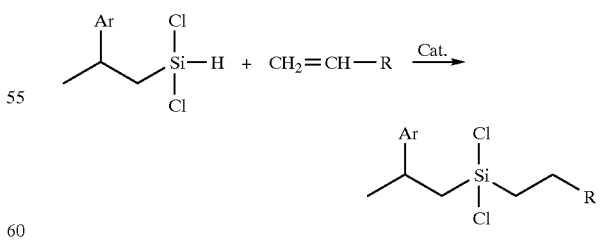

By subjecting the (2-arylpropyl)alkylsilane derivatives to partial reduction according to the present process and then to a hydrosilylation reaction, it becomes possible to prepare new organosilicon compounds to which various alkyl groups have been introduced. Further, the inventors of the present invention invented a catalyst system for olefinic polymerization wherein organosilicon compounds are used as an electron donor. (I. N. Jung, J. S. Han, E. J. Cho, Y. T. Jeong, K. K. Kang, U.S. Pat. No. 5,556,822(1996)).

As an organosilicon compound used as an electron donor, it can be generally mentioned a dialkyldialkoxysilane compound which can be easily prepared by partially reducing alkyltrichlorosilane compound by means of this method of the present invention, and introducing alkyl group through hydrosilylation and then, conducting alcohollization reaction.

A typical reaction process of the present invention comprises reacting chlorosilane compound of the formula (II) with lithiumaluminum hydride in the amount of 30 to 50 mole % of the chlorosilane compound (II) in a flask equipped with a reflux cooling device under nitrogen atmosphere while heating to 100 to 200° C. Optionally, aluminum chloride can be added in the amount of 5 mole % relative to the silane compound. If a chlorosilane compound of the formula (II) cannot be heated above 100° C. due to its low boiling point, it can be reacted in a sealed autoclave made of stainless steel. The reaction state is monitored by a gaseous element analyzer, and when the products reach equibrium state, temperature is decreased, and non-polar solvent such as normal hexane is added so as to solve the products, which then is filtered to remove the solvent, and followed by a distillation under vacuum or atmospheric pressure to isolate the final products.

The invention will be understood more readily with reference to the following examples; however these examples are intended to illustrate the invention and are not to be construed to limit the scope of the invention.

EXAMPLE 1

Partial reduction of 4.4-dichloro-2-phenyl4-siladecane

A two-necked flask of 50 ml capacity, equipped with a condenser was flame-dried and maintained under dry nitrogen. Into this flask were added 5.0 g (0.016 mol) of 4,4-dichloro-2-phenyl-4-siladecane and 0.21 g (0.0055 mol) and stirred for 24 hours while remaining the temperature at 150° C. The completion of the reaction was confirmed by gas chromatography. About 20 ml of hexane was added into the reaction flask, stirred for 10 minutes, and then filtered. The extraction with hexane was repeated twice further, and 0.51 ml (0.0055 mol) of phosphorousoxitrichloride was added ino the total filtrate and then stirred for 30 minutes and filtered again. The temperature of the filtered solution was raised up to 110° C. under atmospheric pressure so as to remove the compounds having low boiling points. The remaining reaction products were distilled under vacuum to obtain a 3.95 g of a mixture of 4-chloro-2-phenyl-4-siladecane (58%) and unreacted 4,4-dichloro-2-phenyl4-siladecane(26%) and 2-phenyl-4-siladecane (13%). The products were identified by gas chromatography/mass spectrometer, and isolated by separation gas chromatography so as to identify their NMR structure.

4-chloro-2-phenyl-4-siladecane $^1$H—NMR(CDCl$_3$, ppm):0.66~0.79[m,2H, SiCH$_2$(CH$_2$)$_4$CH$_3$], 0.88[t,J=6.9 Hz, 3H, Si(CH$_2$)$_5$,CH$_3$], 1.12~1.34(m, 2H, SiCH$_2$), 1.12~1.34[m, 8H, SiCH$_2$(CH$_2$)$_4$CH$_3$], 1.35, 1.36(d,J=6.9 Hz, 3H, CHCH$_3$), 3.05 (hex,J=7.2 Hz. 1H, CHCH$_3$), 4.53~4.54, 4.67~4.69(m,1H, SiH), 7.02~7.32 (m.5H.ArH)

EXAMPLE 2

Partial reduction of 1.1-dichloro-1-chloropentyl-3-phenyl-1-silabutane

In the same method as Example 1, 5.0 g (0.017 mol) of 1,1-dichloro-1-cyclopentyl-3-phenyl-1-silabutane and 0.34 g (0.0090 mol) of lithiumaluminum hydride were put into the flask and stirred for 24 hours while maintaining the temperature at 150° C. 3.89 g of a mixture of 1-cychloropentyl-3-phenyl-1-chloro-1-silabutane (51%) and unreacted 1,1-dichloro-1-cyclopentyl-3-phenyl-1-silabutane (22%) and 1-cyclopentyl-3-phenyl-1-silabutane (9.1%) was obtained after a distillation under vacuum.

1-chloro-1-cyclopentyl-3-phenyl-1-silabutane $^1$H—NMR(CDCl$_3$, ppm): 1.05~1.11[m,1H, cyclic-CH], 1.22~1.45 (m,2H, cyclic-CH$_2$), 1.29~1.34(m,2H, SiCH$_2$), 1.38, 1.34 (d,J=6.9 Hz, 3H, CHCH$_3$), 1.48~1.66(m,4H, cyclic-CH$_2$), 1.69~1.84 (m,2H, cyclic-CH$_2$), 3.09 (hex,J= 7.2 Hz. 1H, CHCH$_3$), 4.46~4.49, 4.63~4.67(m,1H, SiH), 7.12~7.33(m.5H. ArH).

EXAMPLE 3

Partial reduction of 3,3-dichloro-1,5-diphenyl-3-silahexane

In the same method as Example 1, 5.0 g (0.015 mol) of 3,3-dichloro-1,5-diphenyl-3-silahexane and 0.27 g (0.0071 mol) of lithiumaluminum hydride were put into the flask and stirred for 24 hours while maintaining the temperature at 150° C. 3.91 g of a mixture of 1,5-diphenyl-3-chloro-3-silahexane-(53%) and unreacted 3,3-dichloro-1,5-diphenyl-3-silahexane (25%) and 1,5-diphenyl-3-silahexane (13%) was obtained after distillation under vacuum.

3-chloro-1.5-diphenyl-3-silahexane $^1$H—NMR(CDCl$_3$, ppm): 0.98~1.11(m,2H, SiCH$_2$CH$_2$C$_6$H$_5$), 1.35, 1.32 (d,J=6.6 Hz, 3H, CHCH$_3$), 1.23~1.38(m,2H, SiCH$_2$), 2.60~2.76 (m,2H, SiCH$_2$CH$_2$C$_6$H$_5$), 3.01 (hex,J=7.2 Hz. 1H, CHCH$_3$), 4.57, 4.66 (q,J=3 Hz, 1H, SiH), 7.05~7.46(m. 10H. ArH).

EXAMPLE 4

Partial reduction of 3.3-dichloro-1-cyclohexyl-5-phenyl-3-silahexane

In the same method as Example 1, 26 g (0.079 mol) of 1-cyclohexyl- 3,3-dichloro-5-phenyl-3-silahexane and 2.5 g (0.065 mol) of lithiumaluminumhydride were put into the flask and stirred for 24 hours while maintaining the temperature at 150° C. Then, distillation was carried out under vacuum to obtain 15 g of a mixture of 3-chloro-1-cyclohexyl-5-phenyl-3-silahexane (63%) and unreacted 3,3-dichloro-1 -cyclohexyl-5-phenyl-3-silahexane (14%), and 1 -cyclohexyl-5-phenyl-3-silahexane (7%).

3-chloro-1 -cyclohexyl-5-phenyl-3-silahexane $^1$H—NMR(CDCl$_3$, ppm): 0.62~0.70[m,1H, cyclic-CH], 0.82~1.15 (m,4H, SiCH$_2$CH$_2$C$_6$H$_{11}$), 1.11~1.16(m,2H, SiCH$_2$), 1.32(d,J=6.6 Hz, 3H, CHCH$_3$),1.54~1.86(m,10H, cyclic-CH$_2$), 2.94(hex,J=7.2 Hz. 1H, CHCH$_3$), 3.72~3.75, 3.75~3.82(m,1H, SiH), 7.12~7.31(m.5H. ArH).

EXAMPLE 5

Partial reduction of 4.4-dichloro-2-(chlorophenyl)-3-siladecane

In the same method as Example 1, 9.0 g (0.025 mol) of 4,4-dichloro-2-(cyclophenyl)-3-siladecane as a mixture (4-chlorophenyl 67%, 2-chlorophenyl 27%, 3-chlorophenyl 6%) and 0.33 g (0.0086 mol) of lithiumaluminumhydride were put into the flask and stirred for 24 hours while maintaining the temperature at 150° C. Then, distillation was carried out under vacuum to obtain 3.85 g of a mixture of 4-chloro-2-(chlorophenyl)-3-siladecane (56%) and unreacted 4,4-dichloro-2-(chlorophenyl)-3-siladecane (24%), and 2-(cyclophenyl)-3-siladecane (11 %).

4-chloro-2-(4-chlorophenyl)-3-siladecane $^1$H—NMR(CDCl$_3$, ppm): 0.67~0.84[m,2H, SiCH$_2$(CH$_2$)$_4$CH$_3$], 0.87(t,J=6.9 Hz, 3H, Si(CH$_2$)$_5$CH$_3$), 1.12~1.23(m, 2H, SiCH$_2$), 1.14~1.41(m,8H, SiCH$_2$(CH$_2$)$_4$CH$_3$), 1:34, 1.35(d,J=6.9 Hz, 3H, CHCH$_3$), 3.02(hex, J=7.2 Hz, 1H, CHCH$_3$), 4.54~4.55, 4.68~4.70(m,1H, SiH),6.94~7.34 (m.5H. ArH).

4-chloro-2-(2-chlorophenyl)-3-siladecane $^1$H—NMR(CDCl$_3$, ppm): 0.67~0.84[m,2H, SiCH$_2$(CH$_2$)$_4$CH$_3$], 0.87(t,J=6.9 Hz, 3H, Si(CH$_2$)$_5$CH$_3$), 1.12~1.23 (m,2H, SiCH$_2$), 1.14~1.41(m,8H, SiCH$_2$(CH$_2$)$_4$CH$_3$), 1.32, 1.33(d,J=6.9 Hz, 3H, CHCH$_3$), 3.60(hex,J=7.2 Hz, 1H, CHCH$_3$), 4.56~4.57, 4.70~4.72(m, 1H, SiH), 6.94~7.34 (m.5H. ArH).

EXAMPLE 6

Partial reduction of 1,1-dichloro-3-(chlorophenyl)-1-cyclopentyl-1-silabutane

In the same method as Example 1, 9.0 g (0.028 mol) of 1,1-dichloro-3-(chlorophenyl)-1-cyclopentyl-1-silabutane as a mixture (4-chlorophenyl 67%, 2-chlorophenyl 27%, 3-chlorophenyl 6%) and 0.53 g (0.014 mol) of lithiumaluminum hydride were put into the flask and stirred for 24 hours, while maintaining the temperature at 150° C. Then, distillation was carried out under vacuum to obtain 3.87 g of a mixture of 1-chloro-3-(chlorophenyl)-1-cyclopentyl-1-siladecane (53%) and unreacted 1,1-dichloro-3-(chlorophenyl)-1-cyclopentyl-1 -silabutane (20%), and 3-(chlorophenyl)-1-cyclopentyl-1-silbutane (8.2%).

1-chloro-3-(4-chlorophenyl)-1-cyclopentyl-1-silabutane $^1$H—NMR(CDCl$_3$, ppm): 1.07~1.21(m,1H, cyclic-CH), 1.28~1.29(m,2H, cyclic-CH$_2$), 1.29~1.58(m,2H, SiCH$_2$), 1.35, 1.39 (d,J=6.9 Hz, 3H, CHCH$_3$), 1.50~1.76(m,4H, cyclic-CH$_2$), 1.71~1.94 (m,2H, cyclic-CH$_2$), 3.05 (hex,J= 7.2 Hz. 1H, CHCH$_3$), 4.47~4.50, 4.64~4.68(m, 1H, SiH), 6.91~7.36(m.5H. ArH).

1-chloro-3-(2-chlorophenyl)-1 -cyclopentyl-1-silabutane $^1$H—NMR(CDCl$_3$, ppm): 1.07~1.21[m,1H, cyclic-CH], 1.28~1.29 (m,2H, cyclic-CH$_2$), 1.29~1.58(m,2H, SiCH$_2$), 1.33, 1.37 (d,J=6.9 Hz, 3H, CHCH$_3$), 1.50~ 1.76(m,4H, cyclic-CH$_2$), 1.71~1.94 (m,2H, cyclic-CH$_2$), 3.63 (hex,J= 7.2 Hz. 1H, CHCH$_3$), 4.49~4.52, 4.65~4.71(m,1H, SiH), 6.91~7.36(m.5H. ArH).

EXAMPLE 7

Partial reduction of 3,3-dichloro-1-(chlorophenyl)-5-phenyl-3-silahexane

In the same method as Example 1, 9.0 g (0.025 mol) of 3,3-dichloro-1-(chlorophenyl)-5-phenyl-3-silahexane as a mixture (4-chlorophenyl 67%, 2-chlorophenyl 27%, 3-chlorophenyl 6%) and 0.45 g (0.012 mol) of lithiumaluminum hydride were put into the flask and stirred for 24 hours, while maintaining the temperature at 150° C. Then, distillation was carried out under vacuum to obtain 3.78 g of a mixture of 3-chloro-1-(chlorophenyl)-5-phenyl-3-silahexane (54%) and unreacted 3,3-dichloro-1-(chlorophenyl)-5-phenyl-3-silahexane (23%), and 1-(chlorophenyl)-5-phenyl-3-silahexane (10%).

3-chloro-1-(4-chlorophenyl)-5-phenyl-3-silahexane $^1$H—NMR(CDCl$_3$, ppm): 0.99~1.21(m,2H, SiCH$_2$CH$_2$C$_6$H$_5$), 1.27, 1.30(d,J=6.6 Hz, 3H, CHCH$_3$), 1.31~1.43 (m,2H, SiCH$_2$), 2.71~2.77 (m,2H, SiCH$_2$CH$_2$C$_6$H$_5$), 3.04 (hex,J=7.2Hz. 1H, CHCH$_3$), 4.56, 4.61(q,J=3 Hz, 1H, SiH), 7.18~7.48(m.10H. ArH).

3-chloro-1-(2-chlorophenyl)-5-phenyl-3-silahexane $^1$H—NMR(CDCl$_3$, ppm): 0.99~1.21(m,2H, SiCH$_2$CH$_2$C$_6$H$_5$), 1.29, 1.32(d,J=6.6 Hz, 3H, CHCH$_3$ ), 1.31~1.43(m,2H, SiCH$_2$), 2.71~2.77(m,2H, SiCH$_2$CH$_2$C$_6$H$_5$), 3.62(hex,J=7.2Hz. 1H, CHCH$_3$), 4.58, 4.64(q,J=3Hz, 1H, SiH), 7.18~7.48(m.10H. ArH).

EXAMPLE 8

Partial reduction of 3,3-dichloro-5-(chlorophenyl)-1-cyclohexyl1-3-silahexane

In the same method as Example 1, 9.0 g (0.025 mol) of 3,3-dichloro-5-(chlorophenyl)-1-cyclohexyl-3-silahexane as a mixture (4-chlorophenyl 67%, 2-chlorophenyl 27%, 3-chlorophenyl 6%) and 0.76 g (0.020 mol) of lithiumaluminum hydride were put into the flask and stirred for 24 hours, while maintaining the temperature at 150° C. Then, distillation was carried out under vacuum to obtain 3.8 g of a mixture of 3-chloro-5-(chlorophenyl)-1 -cyclohexyl-3-silahexane (62%) and unreacted 3,3-dichloro-5-(chlorophenyl)-1-cyclohexyl-3-silahexane(11%), and 5-(chlorophenyl)-1-cyclohexyl-3-silahexane (8.1%).

3-chloro-5-(4-chlorophenyl)-1-cyclohexyl-3-silahexane $^1$H—NMR(CDCl$_3$, ppm): 0.59~0.67[m,1H, cyclic-CH], 0.83~1.18 (m,4H, SiCH2CH2C$_6$H$_5$), 1.13~1.17 (m,2H, SiCH$_2$) 1.31, 1.34 (d,J=6.6 Hz, 3H, CHCH$_3$), 1.55~1.92 (m,10H, cyclic-CH$_2$), 2.93(hex,J=7.2Hz. 1H, CHCH$_3$), 3.76~3.79, 3.79~3.86(m,1H, SiH), 7.14~7.33(m.5H. ArH).

3-chloro-5-(2-chlorophenyl)-1-cyclohexyl-3-silahexane $^1$H—NMR(CDCl$_3$, ppm): 0.59~0.67[m,1H, cyclic-CH], 0.83~1.18(m,4H, SiCH$_2$CH$_2$C$_6$H$_{11}$), 1.13~1.17 (m,2H, SiCH$_2$) 1.28, 1.32 (d,J=6.6 Hz, 3H, CHCH$_3$), 1.55~1.92 (m,10H, cyclic-CH$_2$), 3.51(hex,J=7.2Hz. 1H, CHCH$_3$), 3.78~3.81, 3.82~3.87(m,1H, SiH), 7.14~7.33(m.5H. ArH).

EXAMPLE 9

Partial reduction of 2-(4-biphenyl)4.4-dichloro4-siladecane

In the same method as Example 1, 5.0 g (0.013 mol) of 2-(4-biphenyl)-4, 4-dichloro4-siladecane and 0.17 g (0.0044 mol) of lithiumaluminumhydride were put into the flask and stirred for 24 hours, while maintaining the temperature at 190° C. Then, distillation was carried out under vacuum to obtain 3.98 g of a mixture of 2-(4-biphenyl)-4-chloro-4-siladecane(53%)and unreacted2-(4-biphenyl)-4,4-dichloro-4-siladecane (28%), 2-biphenyl4-siladecane (18%).

2-(4-biphenyl)4-chloro-4-siladecane

¹H—NMR(CDCl₃, ppm): 0.68~0.82[m,2H, SiCH₂(CH₂)₄CH₃], 0.88(t,J=6.8 Hz, 3H, Si(CH₂)₅CH3), 1.17~1.35(m, 8H, SiCH₂(CH₂)₄CH₃), 1.35~1.39(m,2H, SiCH₂), 1.41(d,J= 6.7 Hz,3H, CHCH₃), 3.1(hex, J=7.2 Hz, 1H, CHCH₃), 4.61~4.68, 4.72~4.81(m, 1H, SiH), 7.25~7.63(m.10H. ArH).

EXAMPLE 10

Partial reduction of 3-(4-biphenyl)-1,1-dichloro-1-cyclopentyl-1-silabutane

In the same method as Example 1, 4.0 9 (0.011 mol) of 3-(4-biphenyl)-1,1-dichloro-1-cyclopentyl-1-silabutane and 0.21 g (0.0055 mol) of lithiumaluminum hydride were put into the flask and stirred for 24 hours, while maintaining the temperature at 190° C. Then, distillation was carried out under vacuum to obtain 2.32 g of a mixture of 3-(4-biphenyl)-1-cychloropentyl-1-silabutane (48%) and unreacted 3-(4-biphenyl)-1,1-dichloro-1-cyclopentyl-1-silabutane (30%),and3-(4-biphenyl)-1 -cyclopentyl-1-silabutane(20%).

3-(4-biphenyl)-1-chloro-1-cyclopentyl-1-silabutane

¹H—NMR(CDCl₃, ppm): 0.85~1.02[m, 1H, cyclic-CH], 1.34~1.38(m,2H, SiCH₂), 1.40 (d,J=6.7 Hz,3H, CHCH₃), 1.12~2.17(m,8H, cyclic-CH₂), 3.10(hex,J=7.2Hz. 1H, CHCH₃), 4.45~4.60, 4.61~4.73(m, 1H, SiH), 7.03~7.60 (m.10H. ArH).

EXAMPLE 11

Partial reduction of 5-(4-biphenyl)-3,3-dichloro-1-phenyl-3-silahexane

In the same method as Example 1, 4.2 g (0.010 mol) of 5-(4-biphenyl)-3,3-dichloro-1-phenyl-3-silahexane and 0.18 g (0.0048 mol) of lithiumaluminum hydride were put into the flask and stirred for 24 hours while maintaining the temperature at 190° C. Then, distillation was carried out under vacuum to obtain 3.05 g of a mixture of 5-(4-biphenyl)-3-chloro-1 -phenyl-3-silahexane (51 %) and unreacted 5-(4-biphenyl)-3,3-dichloro-1-phenyl-3-silahexane (27%), and 5-(4-biphenyl)-1-phenyl-3-silahexane (18%).

5-(4-biphenyl)-3-chloro-1-phenyl-3-silahexane

¹H—NMR(CDCl₃, ppm): 0.92~1.12[m,2H, SiCH₂CH₂C₆H₅), 1.38 (d,J=6.6 Hz, 3H, CHCH₃), 1.28~1.48(m,2H, SiCH₂), 2.57~2.77(m,2H, SiCH₂CH₂C₆H₅), 3.07(hex,J=7.2 Hz, 1H, CHCH₃), 4.58~4.71, 4.72~4.83(m, 1H, SiH), 7.05~7.59(m.15H. ArH).

EXAMPLE 12

Partial reduction of 5-(4-biphenyl)-3, 3-dichloro-1-cyclohexyl-3-silahexane

In the same method as Example 1, 3.4 g (0.0085 mol) of 5-(4-biphenyl)-3, 3-dichloro-1-cyclohexyl-3-silahexane and 0.16 g (0.043 mol) of lithiumaluminum hydride were put into the flask and stirred for 24 hours while maintaining the temperature of 190° C. Then, distillation was carried out under vacuum to obtain 2.4 g of a mixture of 5-(4-biphenyl)-3-chloro-1-cyclohexyl-3-silahexane (43%) and unreacted 5-(4-biphenyl)-3,3-dichloro-1-cyclohexyl-3-silahexane (31%) and 5-(4-biphenyl)-1 -cyclohexyl-3-silahexane (21 %).

5-(4-biphenyl)-3-chloro-1-cyclohexyl-3-silahexane

¹H—NMR(CDCl₃, ppm): 0.62~0.73[m,1H, cyclic-CH], 0.75~1.05 (m,4H, SiCH₂CH₂C₆H₁₁), 1.33~1.39(m,2H, SiCH₂), 1.44(d,J=6.6 Hz, 3H, CHCH₃), 1.52~1.92(m,10H, cyclic-CH₂), 3.1 (hex,J=7.2 Hz. 1H, CHCH₃), 4.59~4.65, 4.69~4.78(m, 1H, SiH), 6.97~7.60(m.10H. ArH).

EXAMPLE 13

Partial reduction of 9-(dichloromethylsilyl)fluoren

In the same method as Example 1, 4.74 g (0.0170 mol) of 9-(dichloromethylsilyl)fluoren and 0.31 g (0.0082 mol) of lithiumaluminum hydride were put into the flask and stirred for 3 hours while maintaining the temperature at 160° C. Then, distillation was carried out under vacuum to obtain 2.65 g of a mixture of 9-(chloromethylsilyl)fluoren(55%) and unreacted 9-(dichloromethylsilyl)fluoren (11 %) and 9-(methylsilyl)fluoren (22.8%).

9-chloromethylsilyl)fluoren

¹H—NMR(CDCl₃, ppm): 0.07(s,3H, SiCH₃), 4.18 (s,1H, SiCH), 4.99(s,1H, SiH), 7.50~7.91(m.8H. ArH).

EXAMPLE 14

Partial reduction of trichloroethylsilane 3.13 ml (0.0237 mol) of trichloroethylsilane, 0.30 g (0.0079mol) of lithiumaluminum hydride, and 0.16 g (0.0012 mol) of aluminum chloride were put into a 10 ml—stainless steel cylinder, sealed and then reacted for 24 hours while maintaining the temperature at 170° C. The data of gas chromatography indicated that the reaction mixture was comprised of dichloroethylsilane(38%), and incomplete reaction trichloroethylsilane(44%) and chloroethylsilane (5.7%).

EXAMPLE 15

Partial reduction of trichlorocyclohexylsilane 2.51 ml (0.0141 mol) of trichlorocyclohexylsilane, 0.36 g (0.0094 mol) of lithiumaluminumhydride, and 0.09 g (0.0007 mol) of aluminum chloride were put into a 10 ml—stainless steel cylinder which was sealed, and reacted for 24 hours while maintaining the temperature at 170° C. The data from Gas chromatography indicated that the reaction mixture was comprised of dichlorocyclohexylsilane (28%), and unreacted trichlorocyclohexylsilane(32%) and chlorocyclohexylsilane (13%).

What is claimed is:

1. A chlorohydrosilane derivatives having a general formula (I) as follows:

$$R^1R^2SiHCl \qquad (I)$$

wherein $R^1$ is (9-fluorene), and $R^2$ is selected from the group consisting of normalhexyl, cyclopentyl, 2-phenylethyl, 2-cyclohexylethyl, and methyl.

2. A method of preparing chlorohydrosilane having a general formula (I) comprising the reaction of chlorosilane of the formula (II) with lithiumaluminum hydride so that chlorosilane of the formula (II) is partially reduced to chlorohydrosilane of the formula (I):

$$R^1R^2SiCl_2 \quad (II)$$

$$R^1R^2SiHCl \quad (I)$$

wherein $R^1$ is selected from the group consisting of
  (i) a straight, branched, or cyclic alkyl group having 1 to 30 carbon atoms and
  (ii) a straight branched, or cyclic alkyl group having 1 to 30 carbon atoms, each having an aromatic group or a heterocyclic group, and $R^2$ is selected from the group consisting of
  (i) a chloro group,
  (ii) a straight, branched, or cyclic alkyl group having 1 to 30 carbon atoms, and
  (iii) a straight, branched, or cyclic alkyl group having 1 to 30 carbon atoms, each having an aromatic group or a heterocyclic group.

3. The method according to claim 2, wherein 20 to 80 mole % of lithiumaluminum hydride is used based on the compound having a general formula (II).

* * * * *